(12) United States Patent
Woehr et al.

(10) Patent No.: US 7,736,339 B2
(45) Date of Patent: Jun. 15, 2010

(54) CATHETER INSERTION DEVICE

(75) Inventors: Kevin Woehr, Felsberg (DE); Kenneth C. Raines, Bethlehem, PA (US)

(73) Assignee: B.Braun Melsungen AG, Melsungen (DE)

( * ) Notice: Subject to any disclaimer, the term of this patent is extended or adjusted under 35 U.S.C. 154(b) by 663 days.

(21) Appl. No.: 10/520,325

(22) PCT Filed: Jul. 2, 2003

(86) PCT No.: PCT/EP03/07073

§ 371 (c)(1),
(2), (4) Date: Sep. 12, 2005

(87) PCT Pub. No.: WO2004/004819

PCT Pub. Date: Jan. 15, 2004

(65) Prior Publication Data

US 2006/0155245 A1 Jul. 13, 2006

(30) Foreign Application Priority Data

Jul. 4, 2002 (DE) .............................. 202 10 394 U

(51) Int. Cl.
*A61M 5/00* (2006.01)
(52) U.S. Cl. .................................. 604/164.08; 604/110
(58) Field of Classification Search ................. 604/110, 604/167, 263, 533, 164
See application file for complete search history.

(56) References Cited

U.S. PATENT DOCUMENTS 3,562,097 A     2/1971   Hazmburg
(Continued)

FOREIGN PATENT DOCUMENTS

DE          30 00 903 A1       1/1980
(Continued)

OTHER PUBLICATIONS

Patent Abstracts of Japan; entitled "Indwelling Puncture Needle With Wing Having Branching Part", Application No. 11-021665, Publication No. 2000-217925; Date of Publication Aug. 8, 2000, Applicant Hanako Medical KK, 3 pgs.

(Continued)

*Primary Examiner*—Kevin C Sirmons
*Assistant Examiner*—Michael J Anderson
(74) *Attorney, Agent, or Firm*—Klein, O'Neill & Singh, LLP

(57) ABSTRACT

The invention relates to a catheter insertion device comprising: an approximately hollow cylindrical catheter sleeve (2), at whose distal end a catheter (4) is attached; a needle sleeve (8) with a hollow needle (9), which is attached thereto and which, when ready for use, extends through the catheter sleeve (2) and the catheter (4), and; a needle protective element (13) that is arranged inside the catheter sleeve (2) while being able to move on the needle (9). Said needle protective element has an engaging section (13c) that engages with an engaging device (9b), which is formed in the vicinity of the needle tip, when the hollow needle is withdrawn from the catheter sleeve (2). A check valve (7, 17) is placed inside the catheter sleeve (2) between the catheter (4) and the needle protective element (13). The hollow needle (9), when ready for use, extends through said check valve, and the check valve automatically closes once the needle is withdrawn.

25 Claims, 3 Drawing Sheets

U.S. PATENT DOCUMENTS

| | | |
|---|---|---|
| 3,601,151 A | 8/1971 | Winnard |
| 4,143,853 A | 3/1979 | Abramson |
| 4,387,879 A * | 6/1983 | Tauschinski ............ 251/149.1 |
| 4,447,230 A | 5/1984 | Gula et al. |
| 4,449,693 A | 5/1984 | Gereg |
| 4,511,359 A | 4/1985 | Vaillancourt |
| 4,512,766 A | 4/1985 | Vailancourt |
| 4,578,063 A | 3/1986 | Inman et al. |
| 4,619,651 A | 10/1986 | Kopfer et al. |
| 4,673,399 A | 6/1987 | Pruett |
| 4,765,588 A | 8/1988 | Atkinson |
| 4,772,266 A | 9/1988 | Groshong |
| 4,795,432 A * | 1/1989 | Karczmer .................... 604/110 |
| 4,809,679 A | 3/1989 | Shimonaka et al. |
| 4,813,938 A * | 3/1989 | Raulerson ................... 604/158 |
| 4,842,591 A | 6/1989 | Luther |
| 4,846,809 A * | 7/1989 | Sims .......................... 604/198 |
| 4,883,461 A | 11/1989 | Sawyer |
| 4,917,668 A * | 4/1990 | Haindl ................... 604/167.03 |
| 4,927,414 A | 5/1990 | Kulli |
| 4,929,235 A | 5/1990 | Merry et al. |
| 4,929,241 A * | 5/1990 | Kulli .......................... 604/263 |
| 4,944,725 A * | 7/1990 | McDonald ............. 604/164.08 |
| 4,950,260 A | 8/1990 | Bonaldo |
| 4,952,207 A | 8/1990 | Lemieux |
| 4,964,854 A | 10/1990 | Luther |
| 4,966,586 A | 10/1990 | Vaillancourt |
| 4,978,344 A | 12/1990 | Dombrowski et al. |
| 5,051,109 A | 9/1991 | Simon |
| 5,053,010 A | 10/1991 | McGary et al. |
| 5,053,014 A | 10/1991 | Van Heugten |
| 5,053,017 A * | 10/1991 | Chamuel .................... 604/192 |
| 5,062,836 A | 11/1991 | Wendell |
| 5,071,413 A | 12/1991 | Utterberg |
| 5,084,023 A | 1/1992 | Lemieux |
| 5,092,840 A | 3/1992 | Healy |
| 5,108,374 A | 4/1992 | Lemieux |
| 5,127,905 A | 7/1992 | Lemieux |
| 5,135,504 A * | 8/1992 | McLees ................. 604/164.08 |
| 5,147,327 A | 9/1992 | Johnson |
| 5,154,703 A | 10/1992 | Bonaldo |
| 5,156,596 A | 10/1992 | Balbierz et al. |
| 5,158,554 A | 10/1992 | Jepson et al. |
| 5,180,370 A | 1/1993 | Gillespie |
| 5,188,607 A | 2/1993 | Wu |
| 5,195,980 A | 3/1993 | Catlin |
| 5,199,947 A | 4/1993 | Lopez et al. |
| 5,215,528 A * | 6/1993 | Purdy et al. ............. 604/164.08 |
| 5,234,410 A | 8/1993 | Graham et al. |
| 5,242,393 A | 9/1993 | Brimhall et al. |
| RE34,416 E | 10/1993 | Lemieux |
| 5,251,873 A | 10/1993 | Atkinson et al. |
| 5,269,771 A | 12/1993 | Thomas et al. |
| 5,279,591 A | 1/1994 | Simon |
| 5,295,657 A | 3/1994 | Atkinson |
| 5,295,658 A | 3/1994 | Atkinson et al. |
| 5,300,033 A | 4/1994 | Miller |
| 5,312,355 A | 5/1994 | Lee |
| 5,322,517 A * | 6/1994 | Sircom et al. ............... 604/198 |
| 5,328,482 A | 7/1994 | Sircom et al. |
| 5,334,158 A * | 8/1994 | McLees ...................... 604/110 |
| 5,334,159 A | 8/1994 | Turkel |
| 5,336,192 A | 8/1994 | Palestrant |
| 5,344,161 A | 9/1994 | Sandgren |
| 5,344,408 A * | 9/1994 | Partika ....................... 604/192 |
| 5,344,414 A | 9/1994 | Lopez et al. |
| 5,352,205 A | 10/1994 | Dales et al. |
| 5,353,837 A | 10/1994 | Faust |
| 5,360,413 A | 11/1994 | Leason et al. |
| 5,380,305 A | 1/1995 | Ghouri |
| 5,405,323 A * | 4/1995 | Rogers et al. |
| 5,409,461 A | 4/1995 | Steinman |
| 5,419,766 A | 5/1995 | Chang et al. |
| 5,439,451 A | 8/1995 | Collinson et al. |
| 5,454,790 A | 10/1995 | Dubrul |
| 5,456,675 A | 10/1995 | Wolbring et al. |
| 5,458,640 A | 10/1995 | Gerrone |
| 5,458,658 A | 10/1995 | Sircom |
| 5,558,651 A | 9/1996 | Crawford et al. |
| 5,562,630 A | 10/1996 | Nichols |
| 5,562,633 A | 10/1996 | Wozencroft |
| 5,584,808 A | 12/1996 | Healy |
| 5,584,809 A | 12/1996 | Gaba |
| 5,601,536 A | 2/1997 | Crawford et al. |
| 5,613,663 A | 3/1997 | Schmidt et al. |
| 5,634,913 A | 6/1997 | Stinger |
| 5,651,772 A | 7/1997 | Arnett |
| 5,662,610 A | 9/1997 | Sircom |
| 5,688,253 A | 11/1997 | Paradis |
| 5,688,254 A | 11/1997 | Lopez et al. |
| 5,699,821 A | 12/1997 | Paradis |
| 5,718,688 A | 2/1998 | Wozencroft |
| 5,725,503 A | 3/1998 | Arnett |
| 5,738,144 A | 4/1998 | Rogers |
| 5,749,857 A | 5/1998 | Cuppy |
| RE35,841 E | 7/1998 | Frank et al. |
| 5,776,116 A | 7/1998 | Lopez et al. |
| 5,779,681 A | 7/1998 | Bonn |
| D397,434 S | 8/1998 | Pike |
| 5,797,897 A | 8/1998 | Jepson et al. |
| 5,817,069 A | 10/1998 | Arnett |
| 5,830,189 A | 11/1998 | Chang |
| 5,851,196 A | 12/1998 | Arnett |
| 5,865,806 A | 2/1999 | Howell |
| 5,879,337 A | 3/1999 | Kuracina et al. |
| 5,911,705 A | 6/1999 | Howell |
| 5,911,710 A | 6/1999 | Barry et al. |
| 5,935,104 A | 8/1999 | Janek et al. |
| 5,954,698 A | 9/1999 | Pike |
| 5,954,708 A | 9/1999 | Lopez et al. |
| 5,967,490 A | 10/1999 | Pike |
| 5,971,957 A | 10/1999 | Luther et al. |
| 6,001,080 A | 12/1999 | Kuracina et al. |
| 6,004,294 A | 12/1999 | Brimhall et al. |
| 6,068,011 A | 5/2000 | Paradis |
| 6,077,244 A * | 6/2000 | Botich et al. ................. 604/110 |
| 6,080,137 A | 6/2000 | Pike |
| 6,117,108 A * | 9/2000 | Woehr et al. ................. 604/110 |
| 6,171,287 B1 | 1/2001 | Lynn et al. |
| 6,203,527 B1 * | 3/2001 | Zadini et al. ................. 604/110 |
| 6,213,978 B1 * | 4/2001 | Voyten .................. 604/164.01 |
| 6,228,060 B1 | 5/2001 | Howell |
| 6,245,048 B1 | 6/2001 | Fangrow, Jr. et al. |
| 6,287,278 B1 * | 9/2001 | Woehr et al. ................. 604/110 |
| 6,352,520 B1 | 3/2002 | Miyazaki |
| 6,379,333 B1 | 4/2002 | Brimhall et al. |
| 6,379,372 B1 | 4/2002 | Dehdashtian et al. |
| 6,443,927 B1 | 9/2002 | Cook |
| 6,443,929 B1 | 9/2002 | Kuracina et al. |
| 6,485,468 B2 | 11/2002 | Vojtasek |
| 6,506,181 B2 | 1/2003 | Meng et al. |
| 6,533,759 B1 | 3/2003 | Watson et al. |
| 6,585,704 B2 | 7/2003 | Luther et al. |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,629,959 B2 | 10/2003 | Kuracina et al. |
| 6,652,486 B2 | 11/2003 | Bialecki et al. |
| 6,652,490 B2 | 11/2003 | Howell |
| 6,692,471 B2 | 2/2004 | Boudreaux |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |

| | | | |
|---|---|---|---|
| 6,764,468 B1 | 7/2004 | East | |
| 6,860,871 B2 | 3/2005 | Kuracina et al. | |
| 6,883,778 B1 | 4/2005 | Newton et al. | |
| 6,902,546 B2 | 6/2005 | Ferguson | |
| 6,916,311 B2 | 7/2005 | Vojtasek | |
| 6,972,002 B2* | 12/2005 | Thorne | 604/164.08 |
| 7,125,396 B2 | 10/2006 | Leinsing et al. | |
| 7,374,554 B2* | 5/2008 | Menzi et al. | 604/110 |
| 2002/0128604 A1* | 9/2002 | Nakajima | 604/164.01 |
| 2003/0199827 A1* | 10/2003 | Thorne | 604/164.08 |
| 2004/0044313 A1 | 3/2004 | Nakajima | |
| 2004/0225260 A1* | 11/2004 | Villa et al. | 604/164.01 |
| 2006/0155245 A1* | 7/2006 | Woehr | 604/164.08 |

FOREIGN PATENT DOCUMENTS

| | | |
|---|---|---|
| DE | 31 00 622 A1 | 4/1980 |
| DE | 32 10 148 A1 | 9/1983 |
| DE | 44 34 569 A1 | 3/1995 |
| DE | 201 04 539 U1 | 1/2002 |
| EP | 0 414 997 A1 | 4/1990 |
| EP | 0 554 841 A1 | 8/1993 |
| EP | 0 747 084 A2 | 12/1996 |
| EP | 0 799 626 A1 | 10/1997 |
| EP | 1 101 508 A2 | 5/2001 |
| EP | 1 101 508 A3 | 8/2001 |
| EP | 1 180 381 A1 | 2/2002 |
| EP | 1 240 916 B1 | 9/2002 |
| EP | 1 374 942 A1 | 1/2004 |
| EP | 1 374 942 B1 | 1/2004 |
| GB | 2 118 440 A | 11/1983 |
| WO | WO 97/45151 | 12/1997 |
| WO | WO 98/53875 | 12/1998 |
| WO | WO 99/26682 | 6/1999 |
| WO | WO 03011381 A1 * | 2/2003 |
| WO | WO 2004/004819 A1 | 1/2004 |

OTHER PUBLICATIONS

Patent Abstracts of Japan; entitled "Safe Indwelling Needle", Application No. 2000-078335, Publication No. 2001-259029, Date of Publication Sep. 25, 2001, Applicant Medikit KK, 7 pgs.

Patent Abstracts of Japan; entitled "Safety Indwelling Needle", Application No. 2000-182911, Publication No. 2002-000727, Date of Publication Jan. 8, 2002, Applicant Medikit KK, 4 pgs.

Patent Abstracts of Japan; entitled "Indwelling Needle Structure", Application No. 2001-363865, Publication No. 2003-175112, Date of Publication Jun. 24, 2003, Applicant Mitsubishi Pencil Co LTD, 5 pgs.

Patent Abstracts of Japan; entitled "Indwelling Needle Structure and Seal Material Used Therefor", Application No. 2005-035112, Publication No. 2005-261938A, Date of Publication Sep. 29, 2005, Applicant JMS Co LTD, 5 pgs.

Patent Abstracts of Japan; entitled "Indwelling Needle", Application No. 2004-143931, Publication No. 2005-323762, Date of Publication Nov. 24, 2005, Applicant Medikit KK, 4 pgs.

Patent Abstracts of Japan; entitled "Indwelling Needle", Application No. JP 1996-040652, Publication No. JP 9206375, Date of Publication Aug. 12, 1997, Applicant Togo Medikit KK, 2 pgs.

"Conical Fittings With 6% (Luer) Taper for Syringes, Needles and Certain Other Medical Equipment—Part 2: Lock fittings," International Standard, ISO 594-2, second edition, 1998, pp. 1-11, Technical Committee ISO/TC 84, Switzerland.

* cited by examiner

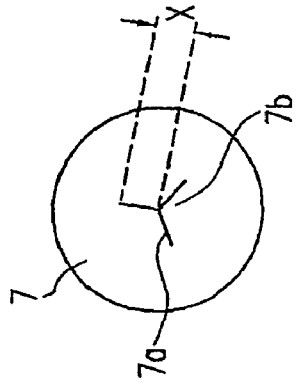
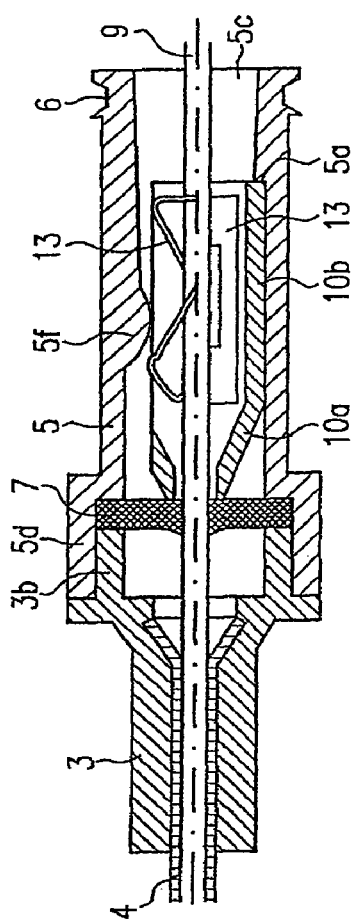
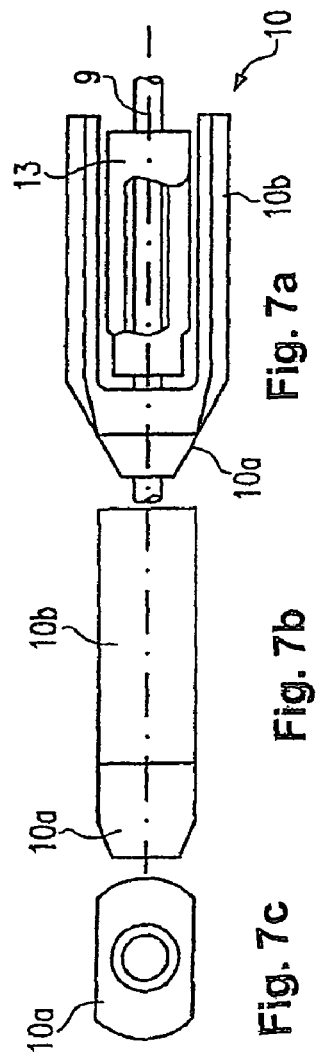

CATHETER INSERTION DEVICE

The invention relates to a catheter insertion device according to the preamble of claim 1.

CROSS-REFERENCE TO RELATED APPLICATION

This is a U.S. national phase application of PCT application No. PCTJEP2003/007073, filed Jul. 2, 2003, which claims priority to German application Ser. No. 202 10 394.3, filed Jul. 4, 2002, the contents of these applications are expressly incorporated herein by reference.

BACKGROUND

A device of this kind is known from EP 352 928, wherein in a hollow catheter hub a needle guard element is arranged. On withdrawal of the hollow needle from the catheter over an engaging means near the tip of the hollow needle, the needle guard element engages with the engaging means and covers the tip when the hollow needle is separated from the catheter. In this design, after withdrawal of the hollow needle from the catheter, through this catheter blood can issue with which the operating personnel can come into contact.

The invention is based on the object of designing a catheter insertion device of the type described above such that an outflow of blood from the catheter is prevented after removal of the hollow needle with the needle guard element.

SUMMARY

This object is solved according to the invention by the features in the characterizing part of claim 1. In the ready position, a check valve is arranged in the catheter hub between the catheter and the needle guard element. Through this valve the hollow needle extends, so that after withdrawal of the hollow needle from the catheter the latter can be reliably closed such that an outflow of blood is prevented, while simultaneously the tip of the hollow needle is securely covered by the needle guard element so that the operating personnel cannot injure themselves on the needle tip.

BRIEF DESCRIPTION OF THE DRAWINGS

Exemplary embodiments of the invention are explained in more detail below with reference to the drawing, in which:

FIG. 5 shows a longitudinal section through another embodiment, FIG. 6 shows a view of the valve disc, FIG. 7 shows different views of a valve actuating element.

DETAILED DESCRIPTION

Figure 1:
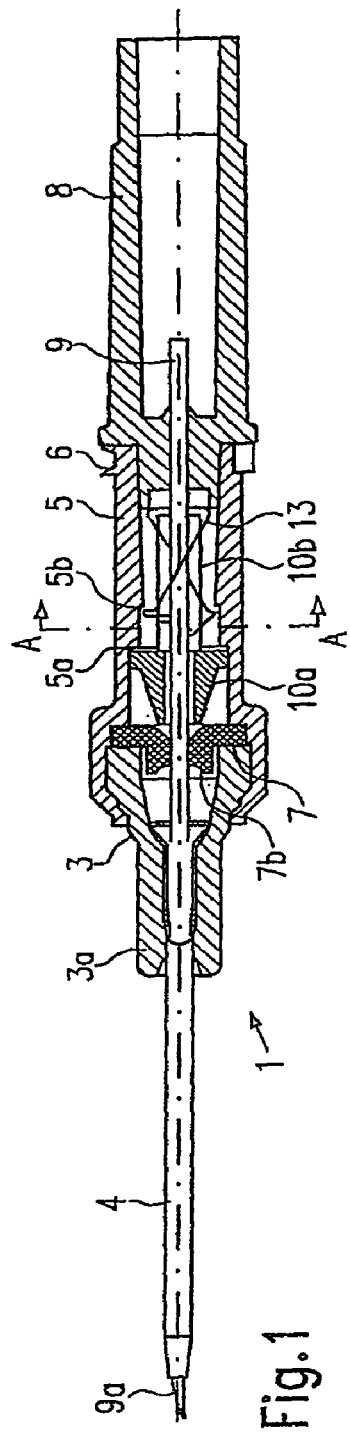
FIG. 1 shows a longitudinal section through a catheter insertion device in the ready position.

FIG. 1 shows a catheter insertion device 1 having a catheter hub 2 which has a two-part form in the embodiment. A distal hub element 3 of the catheter hub has a holding section 3a in which a catheter 4 is press-fitted. The proximal end of the hub element 3 has an enlarged diameter with regard to the distal end and forms a connecting section with a hub element 5 whose distal end overlaps the proximal end of the hub element 3 and which is provided at its proximal end with a Luer thread 6. Between the two hub elements 3 and 5, a check valve in the form of a valve disc 7 is inserted and is fixed in place by the two hub elements 3 and 5.

Figure 3:
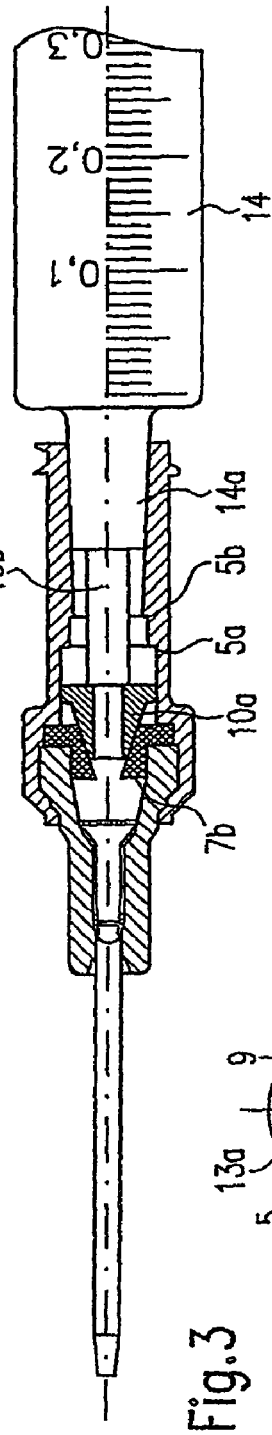
FIG. 3 shows the device with an attached syringe.

In the ready position according to FIG. 1, there is inserted in the catheter hub 2 a needle hub 8 to which a hollow needle 9 is fixed which extends through the valve disc 7 and the catheter 4 so that the needle tip 9a is exposed. Between needle hub 8 and valve disc 7 there is displaceably arranged in the proximal hub element 5 a valve actuating element 10 which has a truncated cone-shaped locating section 10a which serves to open the valve disc 7, as FIG. 3 shows. On the proximal side, a plunger section 10b adjoins the locating section 10a and has a hollow space for receiving a needle guard element 13. In the embodiment shown, the plunger section 10b is formed by two spaced plungers between which the needle guard element in the form of a spring clip 13 is inserted, as shown in the cross-sectional view in FIG. 4.

On withdrawal of the hollow needle 9 from the catheter hub 2, an engaging means 9b (FIG. 2), provided near the needle tip 9a and having the form of a radial projection on the hollow needle which can be formed by light crimping, engages with the outer circumference of a bore in the rear wall 13c of the spring clip 13, so that the spring clip 13 is removed from the catheter hub with the needle 9, while simultaneously the spring arms 13a and 13b of the spring clip cover the needle tip, completely protecting and blocking it. In this separated position shown in FIG. 2, the valve disc 7, due to its elasticity, closes the through-hole for the hollow needle 9 so that no blood can flow out through the catheter 4. As FIG. 6 shows, the valve disc is provided for example with three slits 7a starting from the middle and extending radially over a short section X, forming elastic flaps 7b therebetween which can be expanded by the hollow needle.

FIG. 3 shows the insertion of a syringe 14 in the catheter hub 2, wherein the neck portion 14a of the syringe comes to abut on the plunger section 10b of the valve actuating element 10 and presses it against the valve disc 7, so that the truncated cone-shaped locating section 10a outwardly displaces the flaps 7b of the valve disc and thereby opens the valve, so that a liquid can be inserted from the syringe 14 into the catheter 4.

The incline of the truncated cone on the locating section 10a and the displacement path of the actuating element 10 relative to the valve disc 7 are designed such that due to the elasticity of the material of the valve disc 7, the flaps 7b displace the locating section 10a to the right in FIG. 3 when the syringe 14 is removed from the catheter hub 2. Hereby, the valve disc 7 is automatically closed, as the position in FIG. 2 shows.

Figure 2:
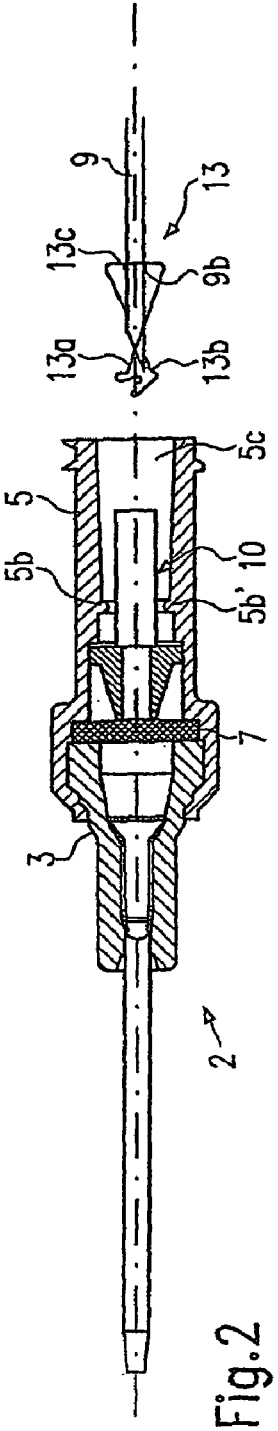
FIG. 2 shows the catheter insertion device with the hollow needle removed.

In the hub element 5, there is formed by a shoulder 5a a stop for the actuating element 10, to define the position of the actuating element in the separated position in FIG. 2. Hereby, the truncated cone-shaped locating section 10a lies near the stop 5a, while its distal end abuts on the valve disc 7 as shown in FIG. 2. The radial slits 7a of the valve disc 7 are designed such that in the ready position in FIG. 1, the flaps 7b are bent radially upwards less than in the open position by the locating section 10a in FIG. 3.

Figure 4:
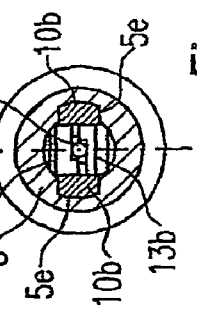
FIG. 4 shows a sectional view along the line A-A in FIG. 1.

As the cross-sectional view in FIG. 4 shows, the two plungers lob of the valve actuating element 10 are guided in longitudinal grooves 5e of the hub element 5 and they project radially inwards into the bore 5c of the hub element 5, so that they form an abutting surface for the neck portion 14a of the syringe 14. The bore 5c in the hub element 5 is formed slightly conically corresponding to the conical neck portion 14a of a syringe.

On the inner circumference of the bore 5c of the hub element 5, a further shoulder 5b having a smaller diameter is formed, on which the radially outer areas of the spring arms 13a and 13b abut in the ready position in FIG. 1. Hereby, the spring clip 13 is fixed in its position in the hub element 5. When the needle hub 8 with the hollow needle 9 is removed from the catheter hub 2, first the spring clip 13 is held on the shoulder 5b by abutting until the radial projection 9b comes to abut on the rear wall 13c of the spring clip. In this position, the two spring arms 13a, 13b can be released from the shoulder 5b and spring back inwards to cover the needle tip, as FIG. 2 shows, whereupon the spring clip 13 with the hollow needle 9 can be removed from the catheter hub.

In the embodiment according to FIGS. 1 to 3, the distal end section of the hub element 5 is shrunk, welded or bonded onto the proximal end section of the hub element 3 after the valve actuating element 10 and the valve disc 7 are inserted in the hub element 5. It is also possible to join the two hub elements 3 and 5 to one another, for example by a thread which is secured against loosening after assembly. The spring clip 13 is inserted together with the hollow needle 9 in the bore 5c of the hub element 5 during assembly, wherein the radially outer areas of the spring arms 13a, 13b snap in at the shoulder 5b under elastic deformation.

Preferably, in front of the shoulder 5b a projection 5b' can be formed in the bore 5c of the hub element, as shown in FIG. 2. Hereby the snap-in and holding effect of the spring clip 13 is increased.

FIG. 5 shows a modified embodiment of the connection of the two hub elements 3 and 5, in which two cylindrical sections 3b and 5d engage in one another. A thread can be provided between these two cylindrical sections. However, it is also possible to bond or weld these two sections.

In this embodiment, the valve actuating element 10 is also modified in relation to the embodiment of FIGS. 1 to 3. FIG. 7a shows a side view of the approximately U-shaped actuating element 10 with the spring clip 13 inserted therein. As the side view rotated by 90° in FIG. 7b shows, the locating section 10a is partly flattened on opposite sides so that the width of the plunger sections 10b extends into the locating section 10a. FIG. 7c is a front view from the left in FIG. 7b and shows the flattened structure of the locating section 10a. FIG. 7d is a sectional view along the central line in FIG. 7b. FIG. 7e shows a section through the valve actuating element 10 along the line B-B in FIG. 7d.

FIG. 5 shows the lower half of the valve actuating element 10 corresponding to the view in FIG. 7a, and the upper half in a sectional view rotated by 90° corresponding to FIG. 7b. The shoulder 5a for positioning the valve actuating element 10 in the hub element 5 is hereby formed on the ends of the diametrically opposite grooves 5e (FIG. 4), so that the proximal ends of the plunger sections 10b abut on the shoulders 5a. Corresponding to the shoulder 5b in FIGS. 1 to 3 in the embodiment in FIG. 5, there is formed on the hub element 5 a projection 5f which projects inwards at diametrically opposite positions on the bore 5c of the hub element 5 and fixes the spring clip 13 in the hub element 5 until the spring arms 13a, 13b spring inwards over the needle tip and the spring clip with the hollow needle 9 is removed from the catheter hub.

Figure 9A:
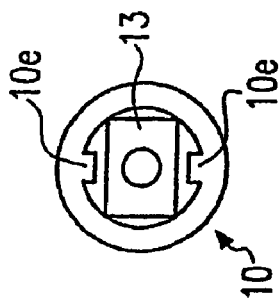
FIG. 9 shows front views of the valve actuating element of FIG. 8.
Figure 8:
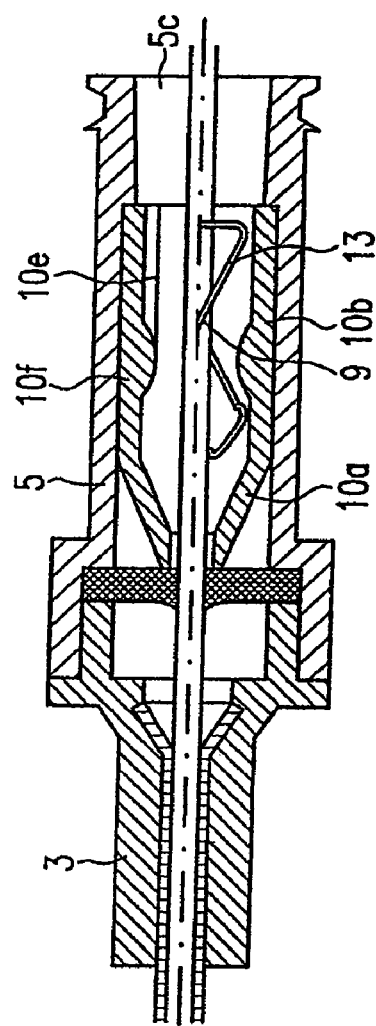
FIG. 8 shows a longitudinal section through a further embodiment.
Figure 9B:
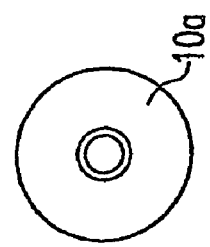

FIG. 8 shows a modified embodiment having a hollow cylindrical valve actuating element 10 on whose inner circumference a projection 10f is formed for positioning the spring clip 13 inside the valve actuating element 10. FIG. 9a shows a front view of the valve actuating element 10 from the right and FIG. 9b shows a front view from the left in FIG. 8, wherein for locating the neck portion 14a of a syringe 14, in this embodiment radially inwardly projecting ribs 10e are formed which protrude radially into the bore 5c of the hub element 5, as the upper half of the valve actuating element in FIG. 8 shows, in which the sectional view of the lower half of the valve actuating element 10 is shown rotated by 90° in relation to the upper half.

Figure 10:
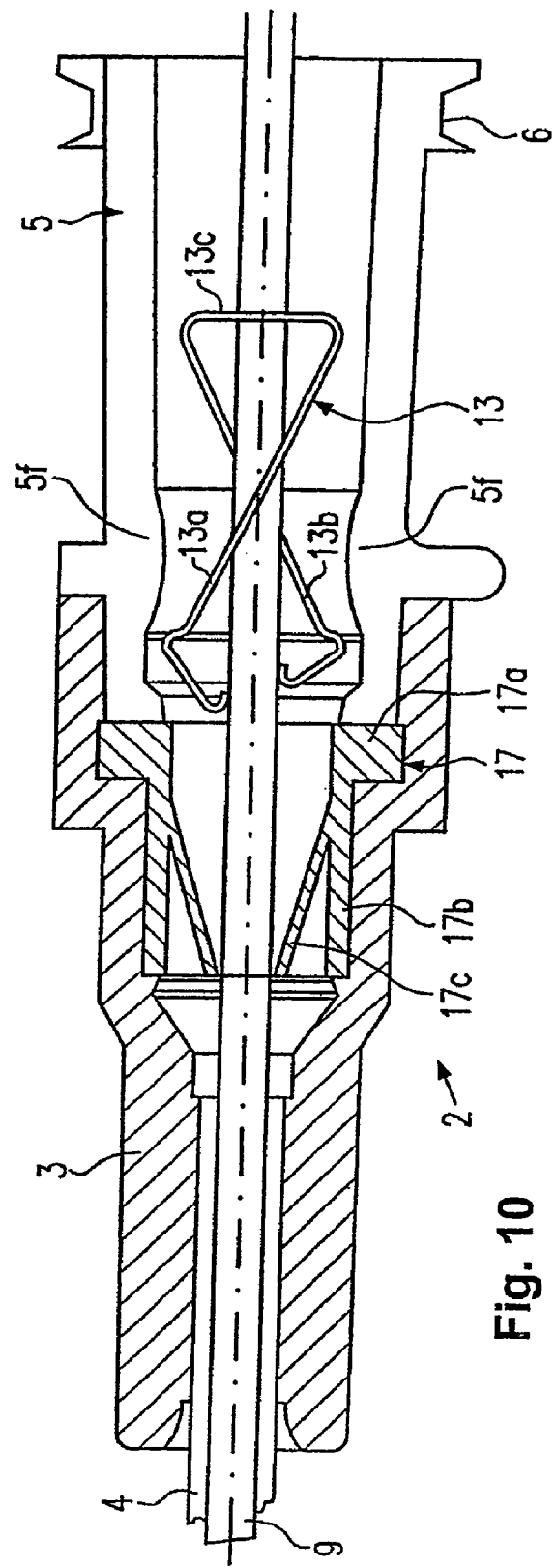
FIG. 10 shows a longitudinal section through a further embodiment.

FIG. 10 shows a modified embodiment wherein between the two hub elements 3 and 5 a check valve 17 is inserted, which has a hollow cylindrical section 17b starting from a flange section 17a and abutting on the inner circumference of the hub element 3. From the inner circumference near the flange section 17a there start two opposite flaps 17c, which abut on the outer circumference of the hollow needle 9 in the ready position in FIG. 10. When the needle 9 is removed from the catheter hub 2, the elastically deformed flaps 17c move inwards and close the valve. In this embodiment, an actuating element for opening the valve 17 is not necessary, because the pressure of the fluid from the syringe 14 displaces the flaps 17c radially outwards so that the liquid can flow out through the valve 17. In this embodiment of a check valve, a so-called duck-bill valve is concerned, whose construction is in itself known.

In FIG. 10, in order to allow the spring clip 13 to be held in the catheter hub during withdrawal of the hollow needle 9 from the catheter hub 2 until the radial projection 9b on the hollow needle engages with the rear wall 13c to cover the needle tip, in this embodiment there is formed on the inner circumference of the proximal hub element 5 a projection 5f which extends radially inwards and on which the radially outer areas of the spring arms 13a and 13b come to abut and hold the spring clip until the spring arms spring back radially inwards to cover the needle tip. The inner diameter of the projection 5f is designed only slightly smaller than the maximum radial dimension at the spring arms 13a and 13b, so that during assembly the spring clip 13 can be inserted by slight pressure into the position in the catheter hub as shown in FIG. 10.

In the embodiment of a catheter insertion device according to FIGS. 1 to 9, in the position of the valve actuating element 10 in FIG. 2 the valve disc 7 can be opened by low pressure produced by the syringe 4 for drawing off liquid from the catheter, wherein the elastic flaps 7b are bent upward by the low pressure. In the embodiment of FIG. 10, a drawing-off of liquid from the catheter is not possible, because the duck-bill valve does not open when there is low pressure on the proximal side.

It is convenient to fabricate the check valve in the form of a valve disc 7 or of the flap valve 17 from elastic silicon, while a correspondingly rigid plastic material is used for the hub elements 3 and 5 and for the valve actuating element 10.

What is claimed is:

1. A catheter insertion device comprising
a hollow catheter hub having a catheter tube attached at a distal end thereof,
a needle hub having a hollow needle attached thereto and extending through the catheter hub and the catheter tube when in a ready position,
a needle guard element arranged displaceably on the needle in the catheter hub and having an engaging section which engages with an engaging means formed near the needle tip when the hollow needle is removed from the catheter hub,
wherein a check valve comprising a valve disc having radial slits starting from a middle section of the valve disc is disposed between the catheter tube and the needle guard element in the catheter hub through which the hollow needle extends in the ready position and which automatically closes after the removal of the needle, and wherein the check valve remains in the catheter hub when the hollow needle is removed from the catheter hub and the catheter tube; and wherein a valve actuating element is displaceably guided in the catheter hub and has a hollow space for receiving the needle guard element.

2. The device according to claim 1, wherein the catheter hub comprises a distal hub element and a proximal hub element, and the check valve is held between the distal hub element and the proximal hub element, which are joined to one another.

3. The device according to claim 1, wherein the check valve has a plurality of radially elastically expandable valve flaps configured to be moved into an open position by fluid pressure generated from a syringe.

4. The device according to claim 1, wherein the catheter hub comprises an inner circumference and a radial projection projecting radially from the inner circumference, which is configured to engage with the needle guard element in the ready position.

5. The device according to claim 1, wherein the valve actuating element is formed as a hollow cylinder with a truncated cone-shaped distal end section and comprising two proximally extending legs defining the hollow space for receiving the needle guard therebetween.

6. The device according to claim 5, wherein the hollow cylindrical valve actuating element comprises an inner circumference and a radial projection.

7. The device according to claim 1, wherein the valve actuating element has a truncated cone-shaped abutting section.

8. The device according to claim 1, wherein the needle guard element is formed as a spring clip which has diametrically opposite spring arms starting from a rear wall provided with a bore, wherein bent end sections of the spring arms overlap and block the needle tip when the engaging means of the needle comes to abut on the rear wall.

9. A catheter insertion device comprising:
a catheter tube attached to an end of a catheter hub, the catheter tube comprising a lumen and the catheter hub comprising an interior cavity;
a needle defining a needle axis attached to an end of a needle hub, said needle projecting through the lumen of the catheter tube;
a valve for regulating fluid flow positioned inside the interior cavity of the catheter hub and in mechanical communication with a movable valve actuating element for opening the valve, and wherein the valve remains inside the interior cavity of the catheter hub when the needle is removed from the catheter tube and the catheter hub; and
a needle guard element comprising two needle guard arms crossing the needle axis of the needle positioned inside the catheter hub adjacent the valve in a ready position.

10. A catheter insertion device comprising:
a catheter tube attached to an end of a catheter hub, the catheter tube comprising a lumen and the catheter hub comprising an interior cavity;
a needle defining a needle axis attached to an end of a needle hub, said needle projecting through the lumen of the catheter tube and comprising an engaging section near a needle tip;
a valve for regulating fluid flow positioned inside the interior cavity of the catheter hub, said valve comprising an opening and the needle projecting through the opening, and wherein the valve remains inside the interior cavity of the catheter hub when the needle is removed from the catheter tube and the catheter hub;

a needle guard element comprising an opening adapted to contact the engaging section of the needle positioned between the valve and the needle hub; and
wherein a valve actuating element is slidably displaced in the interior cavity of the catheter hub for opening the valve.

11. The catheter insertion device of claim 9, wherein the two needle guard arms cross one another.

12. The catheter insertion device of claim 9, wherein the needle guard element comprises a proximal wall comprising an opening having the needle passing therethrough.

13. The catheter insertion device of claim 9, wherein the valve is a disc having at least one slit formed therein.

14. The catheter insertion device of claim 9, wherein the movable valve actuating element comprises two leg sections comprising a space therebetween for accommodating the needle guard.

15. The catheter insertion device of claim 10, wherein the engaging section is crimp.

16. The catheter insertion device of claim 10, wherein the needle guard further comprises at least one arm comprising an apex abutting a shoulder located on the interior surface of the catheter hub.

17. The catheter insertion device of claim 10, wherein the needle guard comprises two arms that intersect one another.

18. The catheter insertion device of claim 10, wherein the valve actuating element comprises two leg sections comprising a space therebetween for accommodating the needle guard.

19. The catheter insertion device of claim 10, wherein the needle guard is made from a metal material.

20. The device according to claim 1, further comprising a valve actuating element formed as a hollow cylinder with a truncated cone-shaped distal end section, with two legs extending proximally therefrom, the two proximally extending legs defining a space therebetween configured for receiving the needle guard element.

21. The device according to claim 20, wherein the catheter hub comprises a diameter variation on an inner circumference of the catheter hub located between a distal end and a proximal end of the valve actuating element.

22. The catheter insertion device according to claim 9, wherein the movable valve actuating element is formed as a hollow cylinder with a truncated cone-shaped distal end section, comprising two proximally extending legs defining a space therebetween configured to receive the needle guard element.

23. The catheter insertion device according to claim 9, wherein the catheter hub comprises a diameter variation on an inner circumference of the catheter hub located between a distal end and a proximal end of the valve actuating element when in the ready position.

24. The catheter insertion device according to claim 10, wherein the valve actuating element is formed as a hollow cylinder with a truncated cone-shaped distal end section, comprising two proximally extending legs defining a space therebetween configured for receiving the needle guard element therebetween.

25. The catheter insertion device according to claim 10, wherein the catheter hub comprises a diameter variation on an inner circumference of the catheter hub located between a distal end and a proximal end of the valve actuating element when in the ready position.

* * * * *

UNITED STATES PATENT AND TRADEMARK OFFICE
CERTIFICATE OF CORRECTION

PATENT NO.        : 7,736,339 B2                                            Page 1 of 1
APPLICATION NO.   : 10/520325
DATED             : June 15, 2010
INVENTOR(S)       : Kevin Woehr et al.

It is certified that error appears in the above-identified patent and that said Letters Patent is hereby corrected as shown below:

In column 2, line 61, delete "lob" and insert -- 10b --, therefor.

Signed and Sealed this

Thirtieth Day of November, 2010

David J. Kappos
*Director of the United States Patent and Trademark Office*